United States Patent [19]

Parsons

[11] Patent Number: 6,107,328
[45] Date of Patent: Aug. 22, 2000

[54] USE OF $5HT_{1B}$ RECEPTOR ANTAGONIST FOR THE TREATMENT OF VASCULAR DISEASE

[75] Inventor: Andrew Parsons, Arlesey, United Kingdom

[73] Assignee: SmithKline Beecham p.l.c., Brentford, United Kingdom

[21] Appl. No.: 09/043,346

[22] PCT Filed: Sep. 9, 1996

[86] PCT No.: PCT/EP96/03989

§ 371 Date: Jul. 1, 1998

§ 102(e) Date: Jul. 1, 1998

[87] PCT Pub. No.: WO97/10824

PCT Pub. Date: Mar. 27, 1997

[30] Foreign Application Priority Data

Sep. 18, 1995 [GB] United Kingdom .................... 9519033

[51] Int. Cl.⁷ ............................ A01N 43/38; A61K 31/40
[52] U.S. Cl. .......................... 514/411; 514/409; 514/410; 514/413
[58] Field of Search ..................................... 514/409, 410, 514/411

[56] References Cited

U.S. PATENT DOCUMENTS 4,814,346  3/1989  Albert et al. ............................ 514/454

FOREIGN PATENT DOCUMENTS

WO 95/11243  4/1995  WIPO .
WO 95/17401  6/1995  WIPO .
WO 96/19477  6/1996  WIPO .

OTHER PUBLICATIONS

:Leonard, B. E., "Sub–types of serotonin receptors: biochemical changes and pharmacological consequences", International Clinical Psychopharmacology, 7, pp. 13–21, 1992.

Hartig, et al., TiPS; vol. 17, 1996, pp. 103–105.

*Primary Examiner*—Dwayne C. Jones
*Attorney, Agent, or Firm*—James M. Kanagy; Charles M. Kinzig

[57] ABSTRACT

The present application is directed to the use of $5HT_{1B}$ or $5HT_{1D}$ receptor antagonists in the treatment of vascular diseases, in particular angina, Raynaud's syndrome, peripheral vascular syndrome or portal hypertension.

4 Claims, No Drawings

USE OF 5HT$_{1B}$ RECEPTOR ANTAGONIST FOR THE TREATMENT OF VASCULAR DISEASE

The present invention relates to a novel method of medical treatment, in particular the treatment and prevention of angina.

EPA 0 533 266/7/8 disclose a series of benzanilide derivatives which are said to possess 5HT$_{1D}$ receptor antagonist activity. These compounds are said to be of use in the treatment of various CNS disorders.

The 5HT$_{1D\beta}$ receptor has now been reclassified as the 5HT$_{1B}$ receptor (P. R. Hartig et al Trends in Pharmacological Science, 1996, 17, 103–105. It has now been found that 5-HT$_{1B}$ receptors are present in smooth muscle. It is expected, as a consequence, that compounds which exhibit 5-HT$_{1B}$ antagonist activity will be useful in treating vascular disease such as angina, Raynaud's syndrome, peripheral vascular disease and portal hypertension.

The present invention therefore provides, in a first aspect, the use of a compound having 5-HT$_{1B}$ antagonist activity in the treatment of vascular disease. Preferred compounds are those which are selective for the 5-HT$_{1B}$ receptor.

Preferred 5-HT$_{1B}$ antagonists include those compounds disclosed in WO 96/1947, that is to say, compounds of formula (I):

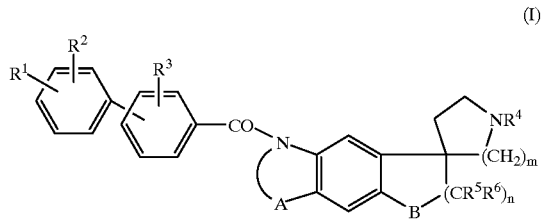

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_{2p}$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and p is 1 to 4; or R$^1$ is an optionally substituted 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl;

R$^5$ and R$^6$ are independently hydrogen or C$_{1-6}$alkyl;

A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$-D where r is 0, 1, 2 or 3 and D is oxygen, sulphur or CR$^{13}$=CR$^{14}$.

B is oxygen, CR$^{15}$R$^{16}$ or NR$^{17}$ where R$^{15}$, R$^{16}$ and R$^{17}$ are independently hydrogen or C$_{1-6}$alkyl or B is S(O)$_b$ where b is 0, 1 or 2;

m is 1, 2 or 3; and n is 1, 2 or 3.

Particularly preferred compounds of formula (I) include 1'-methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine.

Other preferred compounds of the invention include the 5-HT$_{1D}$ antagonists generically and specifically dissolved in WO 95/04729, WO 95/06044, WO95/06644, WO 95/06637, WO 95/11243, WO 95/17401, WO 95/17398, PCT/EP95/0090, PCT/EP95/03226, in particular WO 95/15954, PCT/EP95/01578 and PCT/EP95/01890..

Further preferred compounds of the invention include the 5-HT$_{1B}$ antagonists generically and specifically disclosed in EPA 0 533 266/7/8, GB 2 276 160, GB 2 276 161, GB 2 276162, GB 2 276 163, GB 2 276 164, GB 2 276 165, GB 2 273 930, and WO 94/15920.

Certain compounds exhibiting 5-HT$_{1B}$ antagonist activity are capable of existing in stereoisomeric forms. It will be understood that the invention encompasses all geometric and optical isomers of these compounds and the mixtures thereof including racemates. Tautomers also form an aspect of the invention.

Compounds exhibiting 5-HT$_{1B}$ antagonist activity are capable of existing in stereoisomeric forms. It will be understood that the invention encompasses all geometric and optical isomers of these compounds and the mixtures thereof including racemates. Tautomers also form an aspect of the invention.

Compounds exhibiting 5-HT$_{1B}$ antagonist activity can usually form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic. Salts of 5-HT$_{1B}$ antagonists therefore form an aspect of the invention.

The present invention further provides a method of acute treatment of prophylaxis of vascular disease such as angina, Raynaud's syndrome, peripheral vascular disease and portal hypertension which comprises administering to a host in need thereof an effective amount of a 5-HT$_{1B}$ receptor antagonist or a pharmaceutically acceptable salt thereof. Preferably a 5-HT$_{1B}$ receptor antagonist is used to treat angina.

In a still further aspect, the invention provides the use of a 5-HT$_{1B}$ receptor antagonist or a pharmaceutically acceptable salt thereof in the manufacture of a medicament for the acute treatment or prophylaxis of vascular disease such as angina, Raynaud's syndrome, peripheral vascular disease and portal hypertension.

When used in therapy, the 5-HT$_{1B}$ receptor antagonists are usually formulated in a standard pharmaceutical composition. Such compositions can be prepared using standard procedures.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for examplme, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following examples illustrate the invention.

Description 1
4-(Hydroxymethyl)-1-methyl-1,2,3,6-tetrahydropyridine

To a solution of ethyl 1-methyl-1,2,3,6-tetrahydro-4-pyridinecarboxylate (10.0 ml, 0.061 mole) in THF (200 ml) was added, maintaining temperature below 25° C., lithium aluminum hydride 2.76 g, 0.073 mole). After stirring for a further 15 min, water (2.75 ml), 10% NaOH (4 ml) and water (4 ml) were successively added, and the mixture was filtered. The filtrate was dried ($Na_2SO_4$) and evaporated in vacuo to give the title compound as an amber oil (6.30 g, 81%), which solidified on standing.

$^1$H NMR (200 MHz, $CDCl_3$)

δ(ppm): 5.63 (m, 1H), 4.01 (s, 2H), 2.94 (m, 2H), 2.55 (t, 2H), 2.35 (s, 3H), 2.20 (m, 2H)

Description 2
4-(2-Iodophenoxymethyl)-1-methyl-1,2,3,6-tetrahydropyridine 4-(Hydroxymethyl)-1-methyl-1,2,3,6-tetrahydropyridine (D1, 5.63 g, 0.044 mol), 2-iodophenol (7.80 g, 0.035 mol) and triphenylphosphine (11.61 g, 0.044 mol) were stirred in dry THF (200 ml) under Ar as diethyl azodicarboxylate (7.0 ml, 0.044 mol) was added portionwise. The solution was stirred for 1h, concentrated, diluted with ethyl acetate, and extracted with dil. HCl. The extract was basified (sat. $K_2CO_3$ solution) and extracted with ethyl acetate. This organic extract was dried ($Na_2SO_4$) and evaporated to give a brown oil. Purification by chromatography on silica gel, eluting with 0–10% methanol/chloroform (gradient) gave the title compound (7.65 g, 65%) as an amber oil.

$^1$H NMR (200 MHz, $CDCl_3$)

δ(ppm): 7.76 (dd, 1H), 7.27 (m, 1H), 6.81 (dd, 1H), 6.68 (td, 1H), 5.84 (m, 1H), 4.47 (s, 2H), 2.99 (m, 2H), 2.58 (t, 2H), 2.4–2.25 (m, 5H).

Description 3
2,3-Dihydro-1'-methylspiro[benzofuran-3,4'-piperidine]

4-(2-Iodophenoxymethyl)-1-methyl-1,2,3,6-tetrahydropyridine (D2, 8.72 g, 0.026 mol) and AIBN (0.20 g, 0.0012 mol) were stirred at reflux under Ar in benzene (500 ml) as tributyltin hydride (14.3 ml, 0.053 mol) was added dropwise in benzene (100 ml) over 1 h. The mixture was stirred at reflux for a further 4.5 h, cooled and evaporated. The residue was dissolved in ethyl acetate, and extracted with dil. HCl. The extract was basified (sat. $K_2CO_3$ solution) and extracted with ethyl acetate. This organic extract was dried ($Na_2SO_4$) and evaporated to give a brown solid, which was chromatographed on silica gel, eluting with 0–8% methanol/chloroform (gradient) to give the title compound (3.86 g, 69%) as a light yellow solid.

$^1$H NMR (250 MHz, $CDCl_3$)

δ(ppm): 7.15 (m, 2H), 6.88 (t, 1H), 6.79 (d, 1H), 4.35 (s, 2H), 2.87 (m, 2H), 2.33 (s, 3H), 2.02 (m, 4H), 1.78 (m, 2H)

Description 4
2,3-Dihydro-1'-methyl-5-nitrospiro[benzofuran-3,4'-piperidine]

2,3-Dihydro-1'-methylspiro[benzofuran-3,4'-piperidine] (D3, 2.72 g, 0.013 mol) was dissolved in acetic anhydride (40 ml) and stirred, standing in a cold water bath, as copper nitrate trihydrate (4.30 g, 0.018 mol) was added portionwise over 1h. The mixture was stirred for 16 h, poured into $Na_2CO_3$ solution, treated with excess ammonia solution, and extracted with ethyl acetate. The extract was dried ($Na_2SO_4$) and evaporated to give a brown oil, which was purified by chromatography on silica gel, eluting with 0–5% methanol/dichloromethane (gradient), to give the title compound (1.63 g, 79%) as a yellow-brown solid.

$^1$H NMR (200 MHz, $CDCl_3$)

δ(ppm): 8.11 (dd, 1H), 8.03 (d, 1H), 6.83 (d, 1H), 4,53 (s, 2H), 2.91 (m, 2H), 2.34 (s, 3H), 2.02 (m, 4H), 1.81 (m, 2H).

Description 5
5-Amino-2,3-dihydro-1'-methylspiro[benzofuran-3,4'-piperidine]

2,3-Dihydro-1'-methyl-5-nitrospiro[benzofuran-3,4'-piperidine](D4, 0.98 g, 4.0 mmol) was hydrogenated over 10% palladium on charcoal (0.18 g) in ethanol (50 ml) for 6 h. Catalyst was filtered off onto kieselguhr, and the filtrate was evaporated and chromatographed on silica gel, eluting with 0–25% methanol/chloroform (gradient), to give the title compound (0.52 g, 60%) as a cream solid.

$^1$H NMR (250 MHz, $d^6$DMSO)

δ(ppm): 6.42 (m, 2H), 6.33 (dd, 1H), 4.22 (s, 2H), 2.84 (d, 2H), 2.29 (s, 3H), 2.12 (t, 2H), 1.82 (td, 2H), 1.61 (d, 2H)

Description 6
6-(Cyanomethyl)-2,3-dihydro-1'-methyl-5-nitrospiro[benzofuran-3,4'-piperidine]

2,3-Dihydro-1-methyl-5-nitrospiro[benzofuran-3,4'-piperidine](D4, 0.70 g, 2.8 mmol) and 4-chlorophenoxyacetonitrile (0.90 g, 5.4 mmol) were dissolved in dry DMF (15 ml) and added to potassium t-butoxide (1.60 g, 14.3 mmol). The mixture was stirred under Ar for 6h, diluted with water (150 ml), acidified (5M HCl) and washed with ethyl acetate. It was then basified (saturated K$_2$CO$_3$ solution) and extracted with ethyl acetate. This extract was dried (Na$_2$SO$_4$) and evaporated to give the title compound (0.35 g, 43%) still containing some spirocyclic starting material (ca 30%, NMR).

$^1$H NMR (200 MHz, CDCl$_3$)

δ(ppm): 8.05 (s, 1H), 7.07 (s, 1H), 4.56 (s, 2H), 4.19 (s, 2H), 2.9 (m, 2H), 2.34 (s, 3H), 2.1–1.7 (m, 6H).

Description 7

2,3-Dihydro-1'-methylspiro[furo[2,3-f]indole-3,4'-piperidine]

6-(Cyanomethyl)-2,3-dihydro-1'-methyl-5-nitrospiro[benzofuran-3,4-piperidine](D6, 0.35 g, 1.2 mmol) was hydrogenated at 50 psiH$_2$ over 10% palladium on charcoal (0.30 g) in a mixture of ethanol (18 ml), water (2 ml) and acetic acid (0.15 ml) for 24h. Catalyst was filtered off onto kieselguhr, and the filtrate was evaporated to dryness. Chromatography on silica gel, eluting with 0–12% methanol/chloroform (gradient) gave the title compound (0.020 g, 10%) as a pale orange solid.

$^1$H NMR (250 MHz, CDCl$_2$)

δ(ppm): 8.70 (b, 1H), 7.18 (m, 2H), 6.99 (s, 1H), 6.43 (m, 1H), 4.40 (s, 2H), 3.05 (m, 2H), 2.46 (s, 3H), 2.3–1.7 (m,6H).

Description 8

1'-Methyl-2,3,6,7-tetrahydrospiro[furo[2,3-f]indole-3,4'-piperidine]

2,3-Dihydro-1-methylspiro[furo[2,3-f]indole-3,4'-piperidine](D7, 0.056 g, 0.23 mmol) was stirred in acetic acid (5 ml) as sodium cyanoborohydride (0.044 g, 0.70 mmol) was added portionwise over 10 min. The solution was stirred for 2h, diluted with water (20 ml), basified with saturated K$_2$CO$_3$ solution, and extracted with ethyl acetate. The extract was dried (Na$_2$SO$_4$) and evaporated to give the title compound (0.030 g, 53%), as a white solid.

$^1$H NMR (200 Mhz, CDCl$_3$)

δ(ppm): 6.61 (s, 1H), 6.46 (s, 1H), 4.31 (s, 2H), 3.53 (t, 2H), 2.96 t, 2H), 2.9 (m, 3H), 2.33 (s, 3H), 1.99 (m, 4H), 1.74 (m, 2H).

Description 8—alternative preparation

1'-Methyl-2,3,6,7-tetrahydrospiro[furo[2,3-f]indole-3,4'-piperidine]

(a) A stirred suspension of powdered 1-acetyl-6-bromo-2,3-dihydro-1H-indol-5-ol (Tetrahedron, 1973, 29 (8), 1115) (19 g, 0.074 mole) in dry THF (1700 ml) at room temp. under argon was treated with triphenylphosphine (19.6 g, 0.075 mole) and 1-methyl-1,2,3,6-tetrahydropyridine-4-methanol (J. Med. Chem., 1988, 31, 545)(9.5 g, 0.075 mole), followed by the dropwise addition over 15 mins. of a solution of diethyl azodicarboxylate (11.8 ml, 0.075 mole) in THF (40 ml). A mild exotherm occured and the insoluble material dissolved. The solution was warmed at 32° C. for 1 hour, then concentrated in vacuo to approx. 500 ml volume. The solid which had formed was filtered off and dried affording 16.1 g of beige solid. The filtrate was concentrated in vacuo and the residue treated with ethyl acetate (700 ml) and 1M HCl acid (500 ml), shaken well and the acid layer separated. This was washed with ethyl acetate, then basified with 40% NaOH and extracted with ethyl acetate, followed by chloroform. The combined extracts were dried (Na$_2$SO$_4$) and concentrated in vacuo to leave a yellow solid, which was recrystallised from ethyl acetate (3.8 g) giving a total yield of 19.9 g (74%) of 1-acetyl-6-bromo-2,3-dihydro-5-(pyridin-4-ylmethoxy)-1H-indole.

$^1$H NMR (250 MHz, CDCl$_3$)δ(ppm): 8.42 (s, 1H), 6.72 (s, 1H), 5.80 (br s, 1H), 4.41 (s, 2H), 4.04 (t, 2H), 3.12 (t, 2H), 2.97 (br s, 2H), 2.58 (t, 2H), 2.38 (s, 3H), 2.28 (br s, 2H), 2.18 (s, 3H).

b) A stirred suspension of the product from (a) (20.8 g, 0.057 mole) in benzene (1500 ml) was treated with AIBN (400 mg) and heated to 75° C. under argon, then treated dropwise over 0.5 h with a solution of tributyltin hydride (23 ml, 0.085 mole) in benzene (200 ml). The mixture was heated under reflux for 6 hours, then concentrated in vacuo. The residue was treated with 2M HCl acid (900 ml) and ethyl acetate (600 ml), then shaken well and the acid layer separated, washed with ethyl acetate and then basified with 40% NaOH solution, keeping the temp. below 20° C. A white precipitate was formed which was filtered off, washed with water and dried to afford 14.8 g (91%) of 5-acetyl-1'-methyl-2,3,6,7-tetrahydrospiro[furo[2,3f]indole-3,4'-piperidine].

$^1$H NMR (250 MHz, CDCl$_3$)δ(ppm): 8.11 (s, 1H), 6.60 (s, 1H), 4.36 (s, 2H), 4.03 (t, 2H), 3.10 (t, 2H), 2.92–2.78 (m, 2H), 2.30 (s, 3H), 2.18 (s, 3H), 2.15–1.90 (m, 4H), 1.80–1.63 (m, 2H).

c) A stirred solution of the product from (b)(14.5 g, 0.051 mole) in a mixture of 5M HCl (250 ml) and ethanol (100 ml) was heated under reflux under argon for 2 hours followed by 16 hours at room temp. The ethanol was removed by concentration in vacuo and the remaining solution cooled in an ice bath and basified to pH 12 by addition of 40% NaOH solution. The white precipitate which formed was filtered off, washed with water and dried to afford 6.0 g of the title compound. The filtrate was extracted with ethyl acetate, followed by chloroform. The combined extract was dried (Na$_2$SO$_4$) and concentrated in vacuo leaving a beige solid (6.2 g) and affording a total of 12.2 g (99.9%) of title compound (D8).

Description 9

2'-Methyl-4'-(5-methyl-1,3,4-oxadiazol-2-yl)biphenyl-4-carboxylic acid

A stirred solution of 2-(4-bromo-3-methylphenyl)-5-methyl-1,3,4-oxadiazole (EP 0533268 A1)(0.21 g, 0.0008 mole) in a mixture of DME (10 ml) and water (30 ml) under argon was treated with 4-boronobenzoic acid (0.14 g, 0.0008 mole), sodium carbonate (0.39 g, 0.0037 mole) and tetrakis (triphenylphosphine)palladium (0)(16 mg), then heated under reflux for 4 hours. The mixture was dried (Na$_2$SO$_4$) and concentrated in vacuo to leave the title compound as a white solid (0.19 g, 78%).

$^1$H NMR (250 MHz, CDCl$_3$+d$^6$DMSO) δ(ppm): 8.02 (d, 2H), 7.86 (s, 1H), 7.80 (br d, 1H), 7.32 (d, 2H), 7.27 (d, 1H), 2.54 (s, 3H), 2.26 (s, 3H)

EXAMPLE 1

1'-Methyl-5-(2'-methyl-4'-(5-methyl-1,3,4-oxadiazol-2-yl) biphenyl-4-carbonyl)-2,3,6,7-tetrahydrospiro[furo[2,3-f] indole-3,4'-piperidine]

The title compound was prepared from 1'-methyl-2,3,6,7-tetrahydrospiro[furo[2,3-f]indole-3,4'-piperidine] (D8) and 2'-methyl-4'-(5-methyl-1,3,4-oxadiazol-2-yl)biphenyl-4-carboxylic acid (D9) using the procedure outlined in WO 96/19477 (23%). This was converted to the oxalate salt, which precipitated from acetone/ether as a white solid.

$^1$H NMR (oxalate salt)(250 MHz, d$^6$DMSO) δ(ppm): 7.98–7.80 (m, 3H), 7.72–7.65 (m, 2H), 7.58–7.49 (m, 3H), 6.80 (s, 1H), 4.51 (s, 2H), 4.11–4.04 (m, 4H), 3.09–3.01 (m, 2H), 2.85–2.78 (m, 4H), 2.61 (s, 3H), 2.61–2.55 (m, 2H), 2.50 (s, 3H), 2.38 (s, 3H)

Pharmacological Data

Carotid Vascular Resistance

Cats were anaesthetised with halothane and maintained on choralose 100 mg/kg i.v. Following tracheotomy, the left femoral vein and right femoral artery were cannulated for administration of drugs and measurement of blood pressure respectively. An electromagnetic flow probe (Gould, USA) with an internal diameter of 2 mm was placed around the right carotid artery for continuous recording of carotid blood flow. Carotid blood flow, arterial blood pressure and derived heart rate were displayed on a 6 channel chart recorder (Lectromed, UK) and carotid vascular resistance calculated (mean arterial blood pressure/carotid blood flow).

Sumatriptan (300 ug/kg i.v.) produced a 90% increase in carotid vascular resistance (n=2). 1'-methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] (1 ug/kg i.v) inhibited sumatriptan induced increases in carotid vascular resistance (32%;n=2).

Isolated Tissues

Middle cerebral arteries were removed from two cats anaesthetised with halothane and choralose and scarificed with an overdose of euthatal. Between 3 to 4 ring segments of approximately 5 mm width were obtained from each middle cerebral artery. Artery rings were set up for recording changes in isometric tension, bathed in a Krebs-Henseleit solution maintained at 37° C. and bubbled with 95% oxygen and 5% carbon dioxide. Following responses to 5-HT (100 nmol/L) the effects of sumatriptan were determined on each arterial section. After wash out, the effects of sumatriptan were investigated in the presence or absence of 1'-methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] 100 nmol/L).

1'-methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] produced a parallel rightward shift of the effects of sumatriptan with a concentration ratio of 205 corresponding to a pKb of 9.1.

These data show that $5\text{-HT}_{1D\beta}$ receptors are present in smooth muscle and indicate a therapeutic potential for $5\text{-HT}_{1D\beta}$ antagonists in vascular disease such as angina, Raynaud's syndrome, peripheral vascular disease and portal hypertension.

What is claimed is:

1. A method for the treatment of vascular disease in a host that comprises administering to a subject an effective amount of a $5\text{HT}_{1B}$ receptor antagonist or a pharmaceutically acceptable salt thereof.

2. A method for the treatment of angina, Raynaud's syndrome, peripheral vascular disease or portal hypertension in a host in need thereof that comprises administering to a subject an effective amount of a $5\text{HT}_{1B}$ receptor antagonist or a pharmaceutically acceptable salt thereof.

3. A method for the treatment of vascular disease in a host that comprises administering to a subject an effective amount of a $5\text{HT}_{1B}$ receptor antagonist where the $5\text{HT}_{1B}$ receptor antagonist administered is a compound of formula (I):

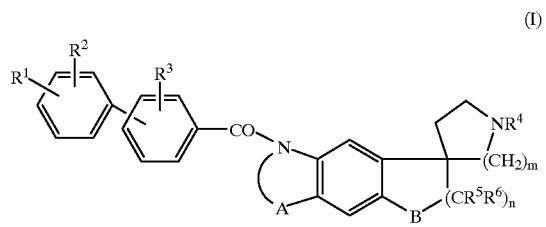

in which $R^1$ is hydrogen, halogen, $C_{1\text{-}6}$-alkyl, $C_{3\text{-}6}$cycloalkyl, $COC_{1\text{-}6}$alkyl, $C_{1\text{-}6}$alkoxy, hydroxy, hydroxy$C_{1\text{-}6}$alkyl, hydroxy$C_{1\text{-}6}$alkoxy, $C_{1\text{-}6}$alkoxy$C_{1\text{-}6}$alkoxy, acyl, nitro, trifluoromethyl, cyano, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1\text{-}6}$alkyl, $CO_2(CH_2)_pOR^{10}$, $CONHNR^{10}R^{11}$, $NR^{10}R^{11}$, $NR^{10}CO_2R^{11}$, $NR^{10}CO(CH_2)_pNR^{10}R^{11}$, $NR^{10}CONR^{10}R^{11}$, $CR^{10}=NOR^{11}$, $CNR^{10}=NOR^{11}$, where $R^9$, $R^{10}$ and $R^{11}$ are independently hydrogen or $C_{1\text{-}6}$alkyl and p is 1 to 4; or $R^1$ is an optionally substituted 5 to 7-membered heterocyclic ring containing 1 to 4 heteroatoms selected from oxygen, nitrogen or sulphur;

$R^2$ and $R^3$ are independently hydrogen, halogen, $C_{1\text{-}6}$alkyl, $C_{3\text{-}6}$cycloalkyl, $C_{3\text{-}6}$cycloalkenyl, $C_{1\text{-}6}$alkoxy, hydroxy$C_{1\text{-}6}$alkyl, $C_{1\text{-}6}$alkylO$C_{1\text{-}6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1\text{-}6}$alkyl;

$R^4$ is hydrogen or $C_{1\text{-}6}$alkyl;

$R^5$ and $R^6$ are independently hydrogen or $C_{1\text{-}6}$alkyl;

A is $(CR^{13}R^{14})_q$ where q is 2, 3 or 4 and $R^{13}$ and $R^{14}$ are independently hydrogen or $C_{1\text{-}6}$alkyl or A is $(CR^{13}R^{14})_r\text{-D}$ were r is 0, 1, 2 or 3 and D is oxygen, sulphur or $CR^{13}=CR^{14}$;

B is oxygen, $CR^{15}R^{16}$ or $NR^{17}$ where $R^{15}$, $R^{16}$ and $R^{17}$ are independently hydrogen or $C_{1\text{-}6}$-alkyl or B is $S(O)_b$ where b is 0, 1 or 2;

m is 1, 2 or 3; and n is 1, 2 or 3.

4. A method for the treatment of vascular disease in a host that comprises administering to a subject an effective amount of a $5\text{HT}_{1B}$ receptor antagonist where the $5\text{HT}_{1B}$ receptor antagonist administered is 1'-methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] or a pharmaceutically acceptable salt thereof.

* * * * *